(12) United States Patent
Bruce et al.

(10) Patent No.: US 10,478,451 B2
(45) Date of Patent: *Nov. 19, 2019

(54) USE OF DEXTRAN SULFATE

(71) Applicant: TX Medic AB, Viken (SE)

(72) Inventors: Lars Bruce, Viken (SE); Adam Bruce, Viken (SE); Anders Waas, Göteborg (SE)

(73) Assignee: TX MEDIC AB, Viken (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/748,519

(22) PCT Filed: Jul. 15, 2016

(86) PCT No.: PCT/SE2016/050720
§ 371 (c)(1),
(2) Date: Jan. 29, 2018

(87) PCT Pub. No.: WO2017/018922
PCT Pub. Date: Feb. 2, 2017

(65) Prior Publication Data
US 2018/0221403 A1 Aug. 9, 2018

(30) Foreign Application Priority Data
Jul. 30, 2015 (SE) ...................................... 1551050

(51) Int. Cl.
*A61K 31/721* (2006.01)
*A61K 31/737* (2006.01)
*A61P 9/10* (2006.01)
*A61P 9/00* (2006.01)
*A61K 9/00* (2006.01)

(52) U.S. Cl.
CPC .......... *A61K 31/721* (2013.01); *A61K 9/0019* (2013.01); *A61K 31/737* (2013.01); *A61P 9/00* (2018.01); *A61P 9/10* (2018.01)

(58) Field of Classification Search
CPC . A61P 9/00; A61P 9/10; A61K 31/721; A61K 31/737
See application file for complete search history.

(56) References Cited

U.S. PATENT DOCUMENTS

| | | | |
|---|---|---|---|
| 5,605,938 A | 2/1997 | Roufa et al. | |
| 6,083,930 A | 7/2000 | Roufa et al. | |
| 6,127,348 A | 10/2000 | Roufa et al. | |
| 6,417,173 B1 | 7/2002 | Roufa et al. | |
| 8,629,123 B2 * | 1/2014 | Nilsson | A61K 31/721 514/59 |
| 2004/0224922 A1 | 11/2004 | King | |
| 2010/0087393 A1 * | 4/2010 | Bansal | A61K 31/737 514/59 |

FOREIGN PATENT DOCUMENTS

| | | |
|---|---|---|
| CN | 102973593 A | 3/2013 |
| WO | 97/22347 A1 | 6/1997 |
| WO | 2008/134430 A1 | 11/2008 |
| WO | 2015/190989 A1 | 12/2015 |

OTHER PUBLICATIONS

Falconer, D. et al "Biosynthesis of dextrans with different molecular weights . . . " Carbohyd. Res., vol. 346, pp. 280-284. (Year: 2011).*
European Search Report dated May 24, 2018 from corresponding European Application No. 16830923.5.
Michael Mahler et al., Differential susceptibility of inbred mouse strains to dextran sulfate sodium-induced colitis, American Journal of Physiology, 274:G544-G551 (Jul. 27, 1998).
Jack P. M. Cleutjens et al, Collagen Remodeling after Myocardial Infarction in the Rat Heart, American Journal of Pathology, vol. 147, No. 2, p. 325-338 (Aug. 1995).
Joel Rosenbloom et. al., Strategies for anti-fibrotic therapies, Biochimica et Biophysica Acta, 1832:1088-1103 (2013).
Yara Banz et al., Locally targeted cytoprotection with dextran sulfate attenuates experimental porcine myocardial ischaemia/reperfusion injury, European Heart Journal, 26:2334-2343 (2005).
Guido Krenning et al., The Origin of Fibroblasts and Mechanism of Cardiac Fibrosis, J. Cell. Physiol., 225:631-637 (2010).
Paul F. Mercer et al., Coagulation and coagulation signalling in fibrosis, Biochimica et Biopysica Acta, 1832:1018-1027 (2013).
Matthew Giannandrea et al., Diverse functions of matrix metalloproteinases during fibrosis, Disease Models & Mechanisms, 7:193-203 (2014).
Masato Ohno et al., Effects of Dextran Sulfate on Pulmonary Radiation Injury, Clinical and Experimental Studies, Nihon Kyobu Shikkan Gakkai Zasshi, 16(10):756-64 (1978) with English Title page, Tables, Figures and Abstract.
Dong Fan et al., Cardiac fibroblasts, fibrosis and extracellular matrix remodeling in heart disease, Fibrogenesis & Tissue Repair, 5:15 (pp. 1-13) (2012).
Clarice ZC Chen et al., Focus on collagen: in vitro systems to study fibrogenesis and antifibrosis—state of the art, Febrogenesis & Tissue Repair, 2:7 (pp. 1-10) (2009).
Razi Khan et al., Fibrosis in heart disease: understanding the role of transforming growth factor-B1 in cardiomyopathy, valvular disease and arrhythmia, Immunology, 118:10-24 (2006).
Miroslav Hock et al., The early effect of dextran sodium sulfate administration on carbachol-induced short-circuit current in distal . . . , Physiological research, 60:921-931 (Dec. 2011).
Sigma, Dextran Sulfate, Sigma Prod. Nos. D7037, D4911, D6924, D3257, D8787, D6001, and D8906, Retrieved from the Internet Sep. 19, 2016.
Sigma-Aldrich, Product Specification D7037, Retrieved from the Internet Sep. 19, 2016.

* cited by examiner

*Primary Examiner* — Leigh C Maier
(74) *Attorney, Agent, or Firm* — Porter Wright Morris & Arthur LLP

(57) ABSTRACT

The present embodiments relate to the use of dextran sulfate formulated for systemic administration for treatment, inhibition or prevention of cardiac fibrosis in a subject.

24 Claims, 2 Drawing Sheets

US 10,478,451 B2

USE OF DEXTRAN SULFATE

TECHNICAL FIELD

The present embodiments generally relate to fibrosis treatment, and in particular to the use of dextran sulfate for treating, inhibiting or preventing cardiac fibrosis in a subject.

BACKGROUND

Fibrosis is a process involving formation of excess fibrous connective tissue in an organ or tissue in a reparative or reactive process. Fibrosis can be a reactive, benign or pathological state. In response to injury the fibrosis process is sometimes referred to scarring.

Physiologically fibrosis involves depositing connective tissue, which can obliterate the architecture and function of the underlying organ or tissue. Fibrosis is similar to the process of scarring in that both involve stimulated cells laying down connective tissue, including collagen and glycosaminoglycans. Macrophages and damaged tissue release transforming growth factor beta (TGFβ) in response to, for instance, inflammation or tissue damage. This in turn stimulates the proliferation and activation of fibroblasts, which deposit connective tissue.

U.S. Pat. No. 5,605,938 discloses that biocompatible anionic polymers, including dextran sulfate with an average molecular weight of about 40,000 to 2,000,000 Da, can inhibit fibrosis, scar formation and surgical adhesions typically in connection with surgery. The anionic polymers are administered locally at the fibrotic lesions or can be soaked onto an organ or implant in the form of a viscous liquid or gel that preferably also comprises an adhesive protein containing dihydroxyphenylalanine (DOPA) and hydroxyl-containing amino acid residues.

CN 102973593 discloses the use of dextran sulfate in preparing a medicament for treating hepatic fibrosis. The document mentions that dextran sulfate inhibits the activation of astrocytes and promotes macrophages to secrete metalloproteinase.

SUMMARY

It is a general objective to treat, inhibit or reduce cardiac fibrosis in a subject.

This and other objectives are met by embodiments as disclosed herein.

An aspect of the embodiments relates to dextran sulfate, or a pharmaceutically acceptable salt thereof, formulated for systemic administration to a subject for use in treating, inhibiting or preventing cardiac fibrosis in the subject.

Another aspect of the embodiments relates to use of dextran sulfate, or a pharmaceutically acceptable salt thereof, for the manufacture of a medicament formulated for systemic administration for treatment, inhibition or prevention of cardiac fibrosis in a subject.

A further aspect of the embodiments relates to a method of treating, inhibiting or preventing cardiac fibrosis in a subject. The method comprises systemically administering dextran sulfate, or a pharmaceutically acceptable salt thereof, to the subject.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

Figure 1:
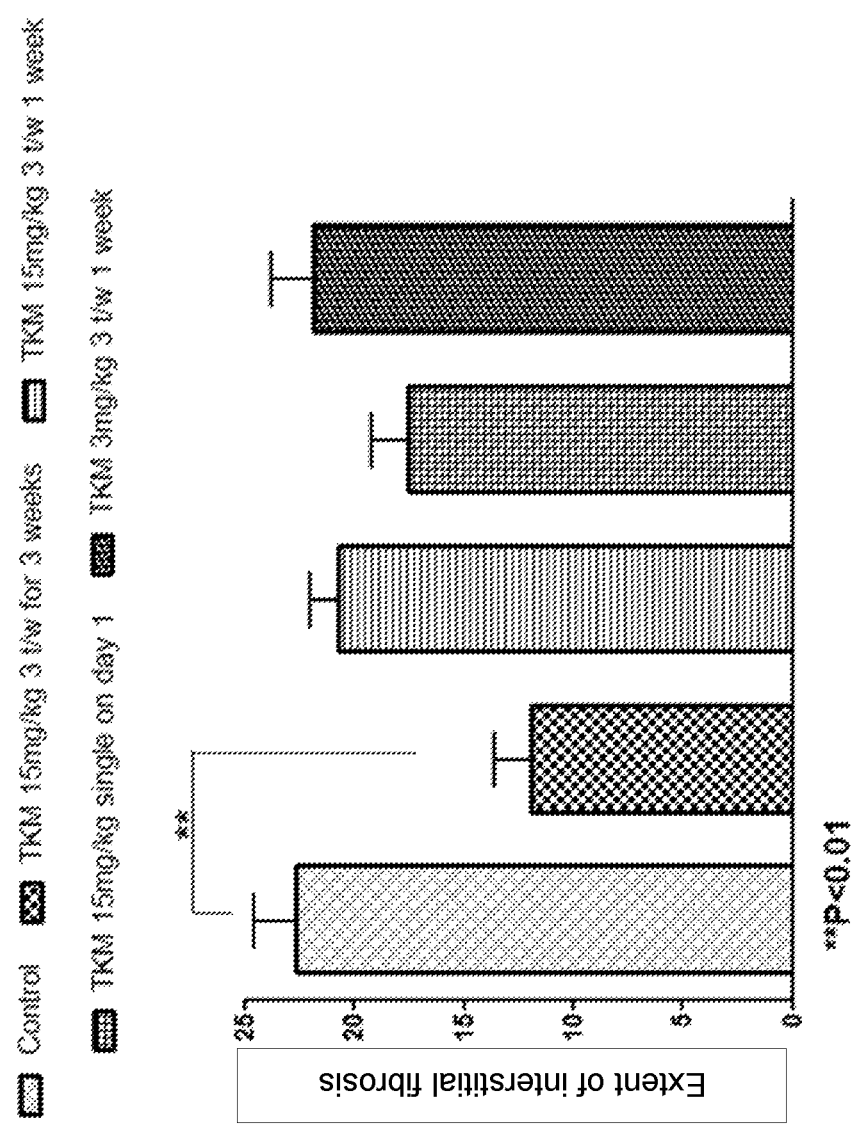
FIG. 1 illustrates estimation of the extent of interstitial fibrosis. Relative area of interstitial fibrosis showed significant suppression of myocardial infarction induced interstitial fibrosis in dextran sulfate group 2M compared to the control group 1M (**$P<0.01$ according to one-way ANOVA followed by Bonferroni post-hoc comparison).

The present embodiments generally relate to fibrosis treatment, and in particular to the use of dextran sulfate for treating, inhibiting or preventing cardiac fibrosis in a subject.

The embodiments are based on the discovery that systemically administered dextran sulfate, or a pharmaceutically acceptable salt thereof, is capable of reducing undesired fibrosis formation in a subject, and in particular reducing or inhibiting such fibrosis formation in ischemic tissue, in particular ischemic cardiac tissue.

Fibrotic diseases include a wide spectrum of medical conditions potentially affecting different organs and tissue in a subject's body. These medical conditions are characterized by elevated expression of genes encoding matrix proteins and the resulting fibrosis disrupts the normal architecture of the affected organ or tissue, ultimately leading to its dysfunction or failure.

The embodiments are capable or treating, inhibiting or preventing cardiac fibrosis in terms of treating, inhibiting or preventing adverse effects of fibrosis diseases by reducing the amount of formed fibrosis in the heart or cardiac tissue. Thus, dextran sulfate of the embodiments is capable of treating, inhibiting or preventing deleterious or injurious cardiac fibrosis.

Accordingly, an aspect of the embodiments relates to dextran sulfate, or a pharmaceutically acceptable salt thereof, formulated for systemic administration to a subject for use in treating, inhibiting or preventing cardiac fibrosis in the subject.

It was highly surprising that systemically delivered dextran sulfate could significantly reduce deleterious fibrosis formation in the light of U.S. Pat. No. 5,605,938. This patent document discloses that dextran sulfate administered locally could inhibit fibrosis and scar formation in connection with, among others, implantation of various implants. It was speculated therein that the negative charges of the dextran sulfate polymer were involved in inhibiting invasions of various cells at the implantation site. In order for such negative charges to have the cell-invasion-inhibiting effect dextran sulfate needs to be administered locally at the desired site. Accordingly, the implant was advantageously coated with dextran sulfate in U.S. Pat. No. 5,605,938.

The experimental data as presented herein shows that dextran sulfate of the embodiments can be systemically administered, i.e. not locally at the target site, and still exert its desired anti-fibrotic effect.

Dextran sulfate, or the pharmaceutically acceptable salt thereof, is formulated for systemic administration to the subject. In an embodiment, dextran sulfate, or the pharmaceutically acceptable salt thereof, is formulated for parenteral administration as an example of systemic administration to achieve a systemic effect in the subject.

Examples of parenteral administration routes include intravenous (i.v.) administration, intra-arterial administration, intra-muscular administration, intracerebral administration, intracerebroventricular administration, intrathecal administration and subcutaneous (s.c.) administration.

In an embodiment, dextran sulfate, or the pharmaceutically acceptable salt thereof, is preferably formulated for intravenous (i.v.) or subcutaneous (s.c.) administration to the subject. Accordingly, i.v. and s.c. administration are preferred examples of systemic administration of dextran sulfate, or the pharmaceutically acceptable salt thereof.

Orally delivered dextran sulfate is known to induce colitis and intestinal fibrosis in mice, rats, hamsters and guinea pigs. Accordingly, systemic administration as used herein preferably excludes oral administration of dextran sulfate, or the pharmaceutically acceptable salt thereof. In a particular embodiment, systemic administration of dextran sulfate, or the pharmaceutically acceptable salt thereof, is a systemic administration other than oral administration, preferably other than enteral administration.

In an embodiment, dextran sulfate, or the pharmaceutically acceptable salt thereof, is formulated as an aqueous injection solution, preferably as an aqueous i.v. or s.c. injection solution. Thus, dextran sulfate, or the pharmaceutically acceptable salt thereof, of the embodiments is preferably formulated as an aqueous injection solution with a selected solvent or excipient. The solvent is advantageously an aqueous solvent and in particular a buffer solution. A non-limiting example of such a buffer solution is a citric acid buffer, such as citric acid monohydrate (CAM) buffer, or a phosphate buffer. For instance, dextran sulfate of the embodiments can be dissolved in saline, such as 0.9% NaCl saline, and then optionally buffered with 75 mM CAM and adjusting the pH to about 5.9 using sodium hydroxide. Also non-buffered solutions are possible, including aqueous injection solutions, such as saline, i.e. NaCl (aq). Furthermore, other buffer systems than CAM and phosphate buffers could be used if a buffered solution are desired.

Dextran sulfate is preferably a so-called low molecular weight dextran sulfate.

In the following, reference to (average) molecular weight and sulfur content of dextran sulfate applies also to any pharmaceutically acceptable salt of dextran sulfate. Hence, the pharmaceutically acceptable salt of dextran sulfate preferably has the average molecular weight and sulfur content as discussed in the following embodiments.

Dextran sulfate is a sulfated polysaccharide and in particular a sulfated glucan, i.e. polysaccharide made of many glucose molecules. Average molecular weight as defined herein indicates that individual sulfated polysaccharides may have a molecular weight different from this average molecular weight but that the average molecular weight represents the mean molecular weight of the sulfated polysaccharides. This further implies that there will be a natural distribution of molecular weights around this average molecular weight for a dextran sulfate sample.

Average molecular weight (Mw) of dextran sulfate is typically determined using indirect methods such as gel exclusion/penetration chromatography, light scattering or viscosity. Determination of average molecular weight using such indirect methods will depend on a number of factors, including choice of column and eluent, flow rate, calibration procedures, etc.

Average molecular weight $$(M_w): \frac{\Sigma M_i^2 N_i}{\Sigma M_i N_i},$$

typical for methods sensitive to molecular size rather than numerical value, e.g. light scattering and size exclusion chromatography (SEC) methods. If a normal distribution is assumed, then a same weight on each side of $M_w$, i.e. the total weight of dextran sulfate molecules in the sample having a molecular weight below $M_w$ is equal to the total weight of dextran sulfate molecules in the sample having a molecular weight above $M_w$.

In an embodiment, dextran sulfate, or the pharmaceutically acceptable salt thereof, preferably has an average molecular weight equal to or below 40000 Da, more preferably equal to or below 20000 Da and in particular equal to or below 10000 Da.

Dextran sulfate of a molecular weight exceeding 10000 Da generally has a lower effect vs. toxicity profile as compared to dextran sulfate having a lower average molecular weight. This means that the maximum dose of dextran sulfate that can be safely administered to a subject is lower for larger dextran sulfate molecules (>10000 Da) as compared to dextran sulfate molecules having an average molecular weight within the preferred range. As a consequence, such larger dextran sulfate molecules are less appropriate in clinical uses when the dextran sulfate is to be systemically administered to subjects in vivo.

In an embodiment, dextran sulfate, or the pharmaceutically acceptable salt thereof, has an average molecular weight within a range of 2000 and 10000 Da. In another embodiment, the average molecular weight is within a range of 2500 and 10000 Da. In a particular preferred embodiment, the average molecular weight is within a range of 3000 to 10000 Da.

In an optional, but preferred embodiment, less than 40% of the dextran sulfate molecules have a molecular weight below 3000 Da, preferably less than 35%, such as less than 30% or less than 25% of the dextran sulfate molecules have a molecular weight below 3000 Da. In addition, or alternatively, less than 20% of the dextran sulfate molecules have a molecular weight above 10000 Da, preferably less than 15%, such as less than 10% or less than 5% of the dextran sulfate molecules have a molecular weight above 10000 Da. Thus, in a particular embodiment, the dextran sulfate has a substantially narrow molecular weight distribution around the average molecular weight.

In a particular embodiment, the average molecular weight of dextran sulfate, or the pharmaceutically acceptable salt thereof, is within a range of 3500 and 9500 Da, such as within a range of 3500 and 8000 Da.

In another particular embodiment, the average molecular weight of dextran sulfate, or the pharmaceutically acceptable salt thereof, is within a range of 4500 and 7500 Da.

In a further particular embodiment, the average molecular weight of dextran sulfate, or the pharmaceutically acceptable salt thereof, is within a range of 4500 and 5500 Da.

Thus, in a currently preferred embodiment the average molecular weight of dextran sulfate, or the pharmaceutically acceptable salt thereof, is preferably approximately 5000 Da or at least substantially close to 5000 Da, such as 5000±500 Da, for instance 5000±400 Da, preferably 5000±300 Da or 5000±200 Da, such as 5000±100 Da. Hence, in an embodiment, the average molecular weight of dextran sulfate, or the pharmaceutically acceptable salt thereof, is 4.5 kDa, 4.6 kDa, 4.7 kDa, 4.8 kDa, 4.9 kDa, 5.0 kDa, 5.1 kDa, 5.2 kDa, 5.3 kDa, 5.4 kDa or 5.5 kDa.

In a particular embodiment, the average molecular weight of dextran sulfate, or the pharmaceutically salt thereof as presented above is average $M_w$, and preferably determined by gel exclusion/penetration chromatography, size exclusion chromatography, light scattering or viscosity-based methods.

In a particular embodiment, dextran sulfate, or the pharmaceutically acceptable salt thereof, consists, on average, of about or slightly above 5 glucose units and has an average sulfate number per glucose unit of at least 2.0, such as of at least 2.5.

Dextran sulfate is a polyanionic derivate of dextran and contains sulfur. The average sulfur content for dextran sulfate of the embodiments is preferably 15 to 20% and more preferably approximately 17%, generally corresponding to about or at least two sulfate groups per glucosyl residue. In a particular embodiment, the sulfur content of dextran sulfate is preferably equal to or at least close to the maximum possible degree of sulfur content of the corresponding dextran molecules.

In a particular embodiment, dextran sulfate of the embodiments has a number average molecular weight ($M_n$) as measured by nuclear magnetic resonance (NMR) spectroscopy within an interval of 1850 and 2000 Da.

In another particular embodiment, dextran sulfate of the embodiments has on average 5.1 glucose units and an average sulfate number per glucose unit of 2.6 to 2.7, typically resulting in a number average molecular weight ($M_n$) as measured by nuclear magnetic resonance (NMR) spectroscopy within an interval of 1850 and 2000 Da.

Number average molecular weight $$(M_n): \frac{\Sigma M_i N_i}{\Sigma N_i},$$

typically derived by end group assays, e.g. NMR spectroscopy or chromatography. If a normal distribution is assumed, then a same number of dextran sulfate molecules can be found on each side of $M_n$, i.e. the number of dextran sulfate molecules in the sample having a molecular weight below $M_n$ is equal to the number of dextran sulfate molecules in the sample having a molecular weight above $M_n$.

A dextran sulfate, or pharmaceutically salt thereof, that can be used according to the embodiments is described in WO 2016/076780.

The dextran sulfate according to the embodiments can be provided as a pharmaceutically acceptable salt of dextran sulfate. Such pharmaceutically acceptable salts include e.g. a sodium or potassium salt of dextran sulfate.

Suitable dose ranges for the dextran sulfate, or the pharmaceutically acceptable salt, of the embodiments may vary according to the size and weight of the subject, the condition for which the subject is treated, and other considerations. In particular for human subjects, a possible dosage range could be from 1 μg/kg to 150 mg/kg of body weight, preferably from 10 μg/kg to 100 mg/kg of body weight.

In preferred embodiments, dextran sulfate, or the pharmaceutically acceptable salt thereof, is formulated to be systemically administered at a dosage in a range from 0.05 to 50 mg/kg of body weight of the subject, preferably from 0.05 or 0.1 to 40 mg/kg of body weight of the subject, and more preferably from 0.05 or 0.1 to 30 mg/kg, or 0.1 to 25 mg/kg or from 0.1 to 15 mg/kg or 0.1 to 10 mg/kg body weight of the subject.

Systemic administration of dextran sulfate, or the pharmaceutically acceptable salt thereof, of the embodiments is preferably initiated as soon as possible after occurrence of an event or condition that may otherwise cause fibrosis and in particular deleterious fibrosis in the subject. For instance, fibrosis often occur following an injury or other condition causing ischemia or a cardiovascular disease in the subject. In such a case, systemic administration of dextran sulfate, or the pharmaceutically acceptable salt thereof, is preferably performed as soon as possible following detection or diagnosis of the injury or other condition causing ischemia or a cardiovascular disease.

Systemic administration of dextran sulfate, or the pharmaceutically acceptable salt thereof, does not necessarily have to be limited to treatment of a present medical condition but could alternatively, or in addition, be used for prophylaxis. In other words, dextran sulfate of the embodiments could be systemically administered to a subject that will undergo a medical procedure, such as surgery, that may cause or induce cardiac fibrosis.

Dextran sulfate, or the pharmaceutically acceptable salt thereof, of the embodiments can be systemically administered at a single administration occasion, such as in the form of a single bolus injection. This bolus dose can be injected quite quickly to the patient but is advantageously infused over time so that the dextran sulfate solution is infused over a few minutes of time to the patient, such as during 5 to 10 minutes or more.

Alternatively, dextran sulfate, or the pharmaceutically acceptable salt thereof, of the embodiments can be systemically administered at multiple, i.e. at least two, occasions during a treatment period. Thus, dextran sulfate of the embodiments could be systemically administered once or at multiple times per day, once or at multiple times per week, once or at multiple times per month as illustrative examples.

In a particular embodiment, dextran sulfate, or the pharmaceutically acceptable salt thereof, is formulated for systemic administration at multiple times, such as 2-5 times, preferably 3 times, a week for multiple consecutive weeks, such as at least 2-5 consecutive, preferably at least 3 consecutive weeks.

In an embodiment, systemic administration of dextran sulfate, or the pharmaceutically acceptable salt thereof, could be initiated as soon as possible following an event or condition causing deleterious fibrosis in the subject, such as soon as possible following an ischemic event or heart infarct as mentioned above. Alternatively, the systemic administration could be initiated at a time period following the event or condition causing deleterious fibrosis. A reason for such a delay in systemic administration is that the fibrosis process generally takes a period of time following a fibrosis causing event or condition. For instance, systemic administration of dextran sulfate, or the pharmaceutically acceptable salt thereof, could be initiated within the first week or from one week following an event or condition causing deleterious fibrosis in the subject.

In an embodiment, the subject is a mammalian subject, preferably a primate, and more preferably human subject. Although the embodiments are in particular directed towards treating, inhibiting or preventing cardiac fibrosis in human subjects, the embodiments may also, or alternatively, be used in veterinary applications. Non-limiting example of animal subjects include primate, cat, dog, pig, horse, mouse, rat.

In an embodiment, the subject is suffering from a disease, condition or disorder causing cardiac fibrosis and in particular detrimental, deleterious or injuries fibrosis. Such detrimental, deleterious or injurious fibrosis causes disruption of the normal architecture of the affected organ or tissue, ultimately leading to its dysfunction and failure. This means that detrimental, deleterious or injurious fibrosis is a pathological state or pathological fibrosis of excess deposition of fibrous tissue that will have a negative and detrimental effect on the organ or tissue where the fibrosis takes place.

Accordingly, in an embodiment, dextran sulfate, or the pharmaceutically acceptable salt thereof, is for use in treating, inhibiting or preventing pathological fibrosis causing excess deposition of fibrous tissue in the heart or cardiac tissue of the subject causing dysfunction of the organ or tissue.

In a particular embodiment, the disease, condition or disorder causing fibrosis is selected from a group consisting of endomyocardial fibrosis, fibrosis following myocardial infarction or atrial fibrosis.

Dextran sulfate, or the pharmaceutically acceptable salt thereof, is thereby used to treat, inhibit or prevent the fibrosis component of any of the above mentioned diseases, conditions or disorders. Accordingly, dextran sulfate, or the pharmaceutically acceptable salt thereof, does not necessarily treat, inhibit or prevent the disease, condition or disorder per se but reduces the fibrosis process and thereby the amount of fibrotic tissue resulting from the disease, condition or disorder.

In an embodiment, dextran sulfate, or the pharmaceutically acceptable salt thereof, formulated for systemic administration is used to treat, inhibit or prevent cardiac fibrosis in a subject suffering from cardiac fibrosis.

The pathological accumulation of extracellular matrix (fibrous connective tissue) is a key contributor to cardiac heart failure (CHF) in both diabetic and non-diabetic patients, resulting in progressive stiffening of the ventricular walls and loss of contractility of the heart. Heart failure is a global health problem, appearing most commonly in patients with previous myocardial infarction (MI). Cardiac remodeling, due to fibrosis, seen in both the infarcted and non-infarcted myocardium is recognized to be a major determinant of the development of impaired ventricular function, leading to a poor prognosis.

Accordingly, fibrosis may occur in heart (cardiac fibrosis) in the form of, for instance, endomyocardial fibrosis, fibrosis following myocardial infarction or atrial fibrosis. Fibrosis often occurs following ischemia at a site in the heart muscle, which may have severe and negative consequences in terms of heart wall stiffening, loss of contractility and cardiac remodeling.

In an embodiment, dextran sulfate, or the pharmaceutically acceptable salt thereof, is for use in treating, inhibiting or preventing cardiac fibrosis in a subject having suffered from myocardial infarction or another ischemic condition in the heart, e.g. myocardial ischemia.

In a particular embodiment, dextran sulfate, or the pharmaceutically acceptable salt thereof, is for use in treating, inhibiting or preventing interstitial fibrosis in an infarct area of a heart of the subject.

Experimental data as presented herein show that dextran sulfate has an anti-fibrosis effect in a myocardial infarction model. Dextran sulfate resulted in significantly less cardiac fibrosis and in particular significantly less interstitial fibrosis in the infarct area of the test subjects.

Fibrosis may also occur in connection with transplantation of the heart or cardiac tissue in a subject. Dextran sulfate, or the pharmaceutically acceptable salt thereof, may accordingly be systemically administered to a subject that will be subject to or has recently been subject to heart or cardiac tissue transplantation. Non-limiting examples of such transplanted cardiac tissue includes heart valves, etc.

Dextran sulfate, or the pharmaceutically acceptable salt thereof, may also be systemically administered to a subject in connection with implantation of a medical device, such as pacemaker, stent, prosthesis, in or in connection with the heart of the subject. Thus, pathological cardiac fibrosis may also occur following implantation of medical devices.

Another aspect of the embodiments relates to use of dextran sulfate, or a pharmaceutically acceptable salt thereof, for the manufacture of a medicament formulated for systemic administration for treatment, inhibition or prevention of cardiac fibrosis in a subject.

A further aspect of the embodiments relates to a method of treating, inhibiting or preventing cardiac fibrosis in a subject. The method comprises systemically administering dextran sulfate, or a pharmaceutically acceptable salt thereof, to the subject.

EXPERIMENTS

Evaluation of Anti-Fibrosis Effect of Dextran Sulfate in a Myocardial Infarction Model The present study assessed the effect of dextran sulfate in inhibiting or reducing fibrosis in a rat model of myocardial infarction (MI).

Materials and Methods

The myocardial infarction model in rat involved ligations of the left coronary artery permanently with an intramural stitch. The surgery caused obstruction of the blood flow and subsequently to severe ischemic damage and cardiac walls infarct.

In total 120 female SD rats having an average body weight of 178 g at study initiation (Day 0) were obtained from Harlan Laboratories, Israel. Animals were fed ad libitum a commercial rodent diet (Teklad Certified Global 18% Protein Diet). Animals had free access to autoclaved and acidified drinking water (pH between 2.5 and 3.5) obtained from the municipality supply. Animals were housed under standard laboratory conditions, air conditioned and filtered (HEPA F6/6) with adequate fresh air supply (minimum air changes/hour). Animals were kept in a climate controlled environment with a temperatures range of 20-24° C. and RH range of 30-70% with 12 hours light and 12 hours dark cycle.

Dextran sulfate with an average molecular weight within a range of 5-7 kDa was dissolved in 0.9% NaCl (saline) (Teva Pharmaceutical Industries Ltd) to be injected subcutaneous at doses of 15 mg/kg or 3 mg/kg.

On the day of surgery the animals were anesthetized with a combination of 90 mg/kg ketamine and 10 mg/kg xylazine, and animals were intubated and mechanically ventilated. In order to induce MI, under anesthesia, the rat chest was opened by left thoracotomy, the pericardium was removed and the proximal left coronary artery was permanently occluded with an intramural stitch (Circulation 2008, 117: 1388-1396). Two hours post-surgery, each animal in all treated groups were injected s.c. with dextran sulfate or saline vehicle according to Table 1.

TABLE 1

Group allocation

| Group | Treatment | Volume | S.C. Administration |
|---|---|---|---|
| 1M (n = 23) | Vehicle control | 0.5 ml/kg | 3 times a week, starting on day 1 for 3 weeks |
| 2M (n = 23) | Dextran sulfate 15 mg/kg | | 3 times a week, starting on day 1 for 3 weeks |
| 3M (n = 26) | Dextran sulfate 15 mg/kg | | 3 times a week, starting on day 1 for 1 week |

TABLE 1-continued

Group allocation

| Group | Treatment | Volume | S.C. Administration |
|---|---|---|---|
| 4M (n = 21) | Dextran sulfate 15 mg/kg | | single dose on day 1 |
| 5M (n = 27) | Dextran sulfate 3 mg/kg | | 3 times a week, starting on day 1 for 1 week |

On day 36 after MI induction, the rats were sacrificed by $CO_2$ inhalation and the hearts were harvested and fixed in buffered formalin solution. Routine paraffin embedding was performed using standard histological procedures.

Masson's Trichrome Staining was used for fibrosis evaluation. The hearts were sectioned transversely into five sections that were imbedded in paraffin. Five paraffin sections at 5 µm were performed on a Lika microtome. All sections were stained according to standard Masson's trichrome protocol. The collagen fibers were stained blue, the nuclei were stained black and the background was stained red. The sections were visualized in a computer-imaging system and infarct size was marked and calculated using the ImageJ program. For each animal, five serial sections including one containing the ligature were analyzed and the mean value of all sections for each heart was treated as one value for statistical analysis.

Statistical analysis was performed by two ways ANOVA for repeated measures, followed by Bonferroni post-hoc test.

Results of Cardiac Fibrosis Analysis

Interstitial fibrosis in the marginal area of the infarct was estimated manually in heart sections stained with Masson's Trichrome Staining. The area of interstitial fibrosis was calculated as the percent of the total area of the left ventricle. For each rat five cross-sections were analyzed. The extent of interstitial fibrosis in the margin zone of the infarct is shown in FIG. 1.

The extent of interstitial fibrosis was significantly lower in the dextran sulfate treated group 2M (11.9±0.9%) as compared to the control vehicle treated group 1M (22.7±1.9%). The extent of interstitial fibrosis was also lower in the other dextran sulfate treated groups 3M-5M, although the difference was not significant.

The effect of dextran sulfate seems to be primarily during the time fibrosis is developing following MI. Accordingly, treatment group 2M comprising treatment with dextran sulfate during 3 weeks significantly decreased fibrosis while the effect in the other groups (3M-5M) with shorter treatment was less pronounced. This seems to be in agreement with the pathogenesis of fibrosis in the rat model of myocardial infarction (*American Journal of Pathology* 1995, 147(2): 325-338). This article discloses that the fibrosis process in infarcted cardiac tissue is regulated differently than fibrosis in dermal wounds and in non-infarcted areas of the heart.

Figure 2C:
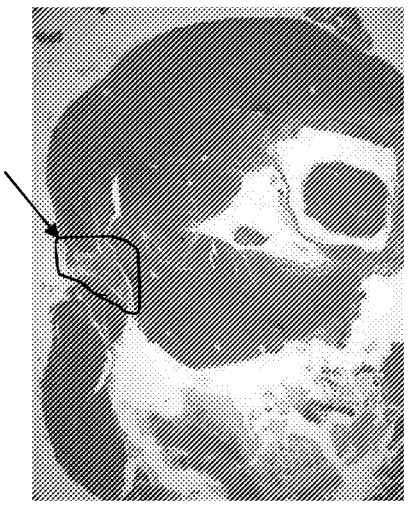
FIGS. 2A-2D are pictures of fibrosis grade in two animals from control group 1M and two animals from dextran sulfate group 2M.
Figure 2D:
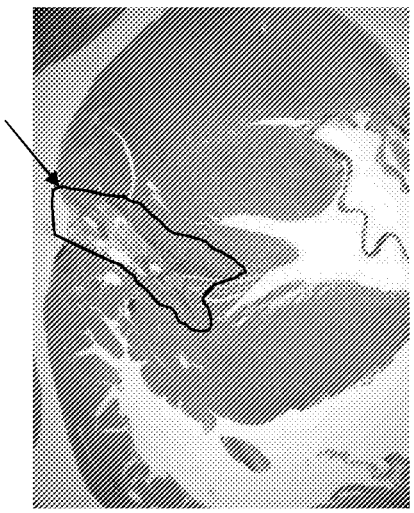
Figure 2A:
Figure 2B:

FIGS. 2A-2D are pictures of fibrosis grade in two animals from group 1M (FIGS. 2A and 2B) and two animals from group 2M (FIGS. 2C and 2D). Fibrotic area stained blue are indicated by arrows in the figures.

The results thereby revealed that dextran sulfate treatment significantly decreased fibrosis at five weeks post-infarction compared to the vehicle control treated group. Dextran sulfate is thereby capable of decreasing the fibrogenesis following myocardial infarction.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A method of treating cardiac fibrosis in a subject, said method comprising systemically administering dextran sulfate, or a pharmaceutically acceptable salt thereof, to a subject suffering from or having a risk of suffering from cardiac fibrosis.

2. The method according to claim 1, wherein systemically administering comprises systemically administering said dextran sulfate, or said pharmaceutically acceptable salt thereof, to a subject having suffered from myocardial infarction or myocardial ischemia.

3. The method according to claim 1, wherein systemically administering comprises intravenously administrating said dextran sulfate, or said pharmaceutically acceptable salt thereof to said subject.

4. The method according to claim 1, wherein systemically administering comprises subcutaneously administrating said dextran sulfate, or said pharmaceutically acceptable salt thereof to said subject.

5. The method according to claim 1, wherein said dextran sulfate, or said pharmaceutically acceptable salt thereof, has an average molecular weight equal to or below 10 000 Da.

6. The method according to claim to 5, wherein said average molecular weight is within a range of 2000 and 10,000 Da.

7. The method according to claim to 6, wherein said average molecular weight is within a range of 3000 and 10,000 Da.

8. The method according to claim 7, wherein said average molecular weight is within a range of 3500 and 9500 Da.

9. The method according to claim 8, wherein said average molecular weight is within a range of 4500 and 7500 Da.

10. The method according to claim 9, wherein said average molecular weight is within a range of 4500 and 5500 Da.

11. The method according to claim 5, wherein said dextran sulfate, or said pharmaceutically acceptable salt thereof, has a number average molecular weight ($M_n$) as measured by nuclear magnetic resonance (NMR) spectroscopy within an interval of 1850 and 2000 Da.

12. The method according to claim 11, wherein said dextran sulfate, or said pharmaceutically acceptable salt thereof, has on average 5.1 glucose units and an average sulfate number per glucose unit of 2.6 to 2.7.

13. The method according to claim 1, wherein said dextran sulfate, or said pharmaceutically acceptable salt thereof, has an average sulfur content in a range from 15 to 20%.

14. The method according to claim 13, wherein said average sulfur content is about 17%.

15. The method according to claim 1, wherein systemically administering comprises systemically administering an aqueous injection solution comprising said dextran sulfate, or said pharmaceutically acceptable salt thereof, to said subject.

16. The method according to claim 1, wherein systemically administering comprises systemically administering said dextran sulfate, or said pharmaceutically acceptable salt thereof, at multiple times a week for multiple consecutive weeks to said subject.

17. The method according to claim 16, wherein systemically administering comprises systemically administering said dextran sulfate, or said pharmaceutically acceptable salt thereof, at 3 times a week for 3 consecutive weeks to said subject.

18. The method according to claim 1, wherein systemically administering comprises systemically administering said dextran sulfate, or said pharmaceutically acceptable salt thereof, at a dosage in a range from 0.05 to 50 mg/kg of body weight of said subject.

19. The method according to claim 18, wherein systemically administering comprises systemically administering said dextran sulfate, or said pharmaceutically acceptable salt thereof, at a dosage in a range from 0.05 to 30 mg/kg of body weight of said subject.

20. The method according to claim 19, wherein systemically administering comprises systemically administering said dextran sulfate, or said pharmaceutically acceptable salt thereof, at a dosage in a range from 0.1 to 15 mg/kg body weight of said subject.

21. The method according to claim 20, wherein systemically administering comprises systemically administering said dextran sulfate, or said pharmaceutically acceptable salt thereof, at a dosage in a range from 0.1 to 10 mg/kg body weight of said subject.

22. The method according to claim 1, wherein said subject is suffering from a disease or disorder selected from a group consisting of endomyocardial fibrosis, fibrosis following myocardial infarction and atrial fibrosis.

23. The method according to claim 1, wherein systemically administering comprises systemically administering said dextran sulfate, or said pharmaceutically acceptable salt thereof, to said subject for treating interstitial fibrosis in an infarct area of a heart of said subject.

24. The method according to claim 1, wherein said pharmaceutically acceptable salt thereof is a sodium salt of dextran sulfate.

* * * * *

UNITED STATES PATENT AND TRADEMARK OFFICE
CERTIFICATE OF CORRECTION

PATENT NO. : 10,478,451 B2
APPLICATION NO. : 15/748519
DATED : November 19, 2019
INVENTOR(S) : Lars Bruce et al.

Page 1 of 1

It is certified that error appears in the above-identified patent and that said Letters Patent is hereby corrected as shown below:

On the Title Page

Item (30), change "1551050" to --1551050-6--.

Signed and Sealed this
Twenty-fifth Day of February, 2020

Andrei Iancu
*Director of the United States Patent and Trademark Office*